United States Patent [19]

Baltimore et al.

[11] Patent Number: 4,719,177

[45] Date of Patent: Jan. 12, 1988

[54] PRODUCTION OF COMPLEMENTARY DNA REPRESENTING RNA VIRAL SEQUENCES BY RECOMBINANT DNA METHODS AND USES THEREFOR

[75] Inventors: David Baltimore, Cambridge; Vincent R. Racaniello, Boston, both of Mass.

[73] Assignee: Massachusetts Institute of Technology, Cambridge, Mass.

[21] Appl. No.: 320,525

[22] Filed: Nov. 12, 1981

Related U.S. Application Data

[63] Continuation-in-part of Ser. No. 255,879, Apr. 20, 1981, abandoned.

[51] Int. Cl.$^4$ .................. C12P 19/34; C12N 15/00; C12N 1/20; C12N 1/00
[52] U.S. Cl. ..................................... 435/91; 435/172.3; 435/235; 435/236; 435/239; 435/253; 435/847; 435/327; 536/27; 935/12; 935/19; 935/21; 935/18; 935/22; 935/56; 935/65; 935/73
[58] Field of Search .................. 435/172.3, 317, 236, 435/239, 4, 5, 7, 8, 9, 91, 235, 253; 935/12, 21, 18, 56, 65, 73, 19; 536/27

[56] References Cited

U.S. PATENT DOCUMENTS

4,237,224 12/1980 Cohen et al. .................. 435/172

FOREIGN PATENT DOCUMENTS

40922 12/1981 European Pat. Off. .......... 435/172.3
48455 3/1982 European Pat. Off. .......... 435/172.3
65924 12/1982 European Pat. Off. .......... 435/172.3
68693 1/1983 European Pat. Off. .......... 435/172.3

OTHER PUBLICATIONS

Luria, *General Virology*, 1976, Wily & Sons, NY, 3rd Ed., pp. 312-315.
Kitamura, et al., Sequence of 1060 3'-terminal nucleotides of polio virus RNA a determined by a modification of the dideozynucleotide method, *Proc. Natl. Acad. Sci.*, vol. 77, 1980, pp. 3196-3200.
Watson, *Molecular Biology of the Gene*, 1977, Benjamin Inc., London, 1977, pp. 655-656 and 591-592.
Nature, vol. 289, No. 5798, Feb. 12, 1981, pp. 555-559, H. Kupper et al.: "Cloning of cDNA of major antigen of foot and mouth disease virus and expression in *E. coli*".
Science, vol. 214, Nov. 20, 1981, pp. 916-919, V. R. Racaniello et al.: "Cloned Poliovirus Complementary DNA Is Infectious In Mammalian Cells".
Proc. Natl. Acad. Sci. USA, vol. 73, No. 7, Jul. 1976, D. L. Kacian et al.: "Synthesis of extensive, possibly complete, DNA copies of poliovirus RNA in high yields and at high specific activities".
Porter et al. (1978), *Nature* (London), 276, 298-301.
Taylor et al. (1976), *Biochem. Biophys. Acta* 442, 324-330.
Racaniello et al. (1981). *Proc. Nat'l Acad. Sci. USA* 78(g), 4887-4891.

*Primary Examiner*—Christine M. Nucker
*Attorney, Agent, or Firm*—Hamilton, Brook, Smith & Reynolds

[57] ABSTRACT

Methods for producing RNA viral cDNA, such as poliovirus ds cDNA, products thereof, and uses thereof, are described. Poliovirus cDNA is produced, for example, by reverse transcribing poliovirus RNA and subsequently inserting the poliovirus cDNA into bacterial plasmids by genetic-engineering techniques. Transformed bacteria are then cloned and cultured to produce replicated chimeric plasmids containing the cDNA poliovirus. Such poliovirus cDNA is useful in assaying for the presence of poliovirus and in the production of antibodies against poliovirus. It has also been found that full-length poliovirus cDNA is infectious, which means it can be employed in producing altered virus particles for vaccines.

21 Claims, 5 Drawing Figures

FIG.5A

```
         10              20              30              40
    TTAAACAGC     TCTGGGGTTG     TACCCACCCC     AGAGGCCCAC
         50              60              70              80
    GTGGCGGCTA    GTACTCCGGT     ATTGCGGTAC     CCTTGTACGC
         90             100             110             120
    CTGTTTTATA    CTCCCTTCCC     GTAACTTAGA     CGCACAAAAC
        130             140             150             160
    CAAGTTCAAT    AGAAGGGGGT     ACAAACCAGT     ACCACCACGA
        170             180             190             200
    ACAAGCACTT    CTGTTTCCCC     GGTGATGTCG     TATAGACTGC
        210             220             230             240
    TTGCGTGGTT    GAAAGCGACG     GATCCGTTAT     CCGCTTATGT
        250             260             270             280
    ACTTCGAGAA    GCCCAGTACC     ACCTCGGAAT     CTTCGATGCG
        290             300             310             320
    TTGCGCTCAG    CACTCAACCC     CTTAGGCTGA     CAGAGTGTAG
        330             340             350             360
    TGAGTCTGGA    CATCCCTCAC     CGGTGACGGT     GGTCCAGGCT
        370             380             390             400
    GCGTTGGCGG    CCTACCTATG     GCTAACGCCA     TGGGACGCTA
        410             420             430             440
    GTTGTGAACA    AGGTGTGAAG     AGCCTATTGA     GCTACATAAG
        450             460             470             480
    AATCCTCCGG    CCCCTGAATG     CGGCTAATCC     CAACCTCGGA
        490             500             510             520
    GCAGGTGGTC    ACAAACCAGT     GATTGGCCTG     TCGTAACGCG
        530             540             550             560
    CAAGTCCGTG    GCGGAACCGA     CTACTTTGGG     TGTCCGTGTT
        570             580             590             600
    TCCTTTTATT    TTATTGTGGC     TGCTTATGGT     GACAATCACA
        610             620             630             640
    GATTGTTATC    ATAAAGCGAA     TTGGATTGGC     CATCCGGTGA
        650             660             670             680
    AAGTGAGACT    CATTATCTAT     CTGTTTGCTG     GATCCGCTCC
        690             700             710             720
    ATTGAGTGTG    TTTACTCTAA     GTACAATTTC     AACAGTTATT
        730             740
    TCAATCAGAC    AATTGTATCA     TA
```

FIG.5B

```
VP4        751
MET GLY ALA GLN VAL SER SER GLN LYS VAL
ATG GGT GCT CAG GTT TCA TCA CAG AAA GTG
           781
GLY ALA HIS GLU ANS SER ASN ARG ALA TYR
GGC GCA CAT GAA AAC TCA AAT AGA GCG TAT
           811
GLY GLY SER THR ILE ASN TYR THR THR ILE
GGT GGT TCT ACC ATT AAT TAC ACC ACC ATT
           841
ASN TYR TYR ARG ASP SER ALA SER ASN ALA
AAT TAT TAT AGA GAT TCA GCT AGT AAC GCG
           871
ALA SER LYS GLN ASP PHE SER GLN ASP PRO
GCT TCG AAA CAG GAC TTC TCT CAA GAC CCT
           901
SER LYS PHE THR GLU PRO ILE LYS ASP VAL
TCC AAG TTC ACC GAG CCC ATC AAG GAT GTC
           931                      →VP2
LEU ILE LYS THR ALA PRO MET LEU ASN SER
CTG ATA AAA ACA GCC CCA ATG CTA AAC TCG
           961
PRO ASN ILE GLU ALA CYS GLY TYR SER ASP
CCA AAC ATA GAG GCT TGC GGG TAT AGC GAT
           991
ARG VAL LEU GLN LEU THR LEU GLY ASN SER
AGA GTA CTG CAA TTA ACA CTG GGA AAC TCC
           1021
THR ILE THR THR GLN GLU ALA ALA ASN SER
ACT ATA ACC ACA CAG GAG GCG GCT AAT TCA
           1051
VAL VAL ALA TYR GLY ARG TRP PRO GLU TYR
GTA GTC GCT TAT GGG CGT TGG CCT GAA TAT
           1081
LEU ARG ASP SER GLU ALA ASN PRO VAL ASP
CTG AGG GAC AGC GAA GCC AAT CCA GTG GAC
```

FIG.5C

```
        1111
GLN PRO THR GLU PRO ASP VAL ALA ALA CYS
CAG CCG ACA GAA CCA GAC GTC GCT GCA TGC
        1141
ARG PHE TYR THR LEU ASP THR VAL SER TRP
AGG TTT TAT ACG CTA GAC ACC GTG TCT TGG
        1171
THR LYS GLU SER ARG GLY TRP TRP TRP LYS
ACG AAA GAG TCG CGA GGG TGG TGG TGG AAG
        1201
LEU PRO ASP ALA LEU ARG ASP MET GLY LEU
TTG CCT GAT GCA CTG AGG GAC ATG GGA CTC
        1231
PHE GLY GLN ASN MET TYR TYR HIS TYR LEU
TTT GGG CAA AAT ATG TAC TAC CAC TAC CTA
        1261
GLY ARG SER GLY TYR THR VAL HIS VAL GLN
GGT AGG TCC GGG TAC ACC GTG CAT GTA CAG
        1291
CYS ASN ALA SER LYS PHE HIS GLN GLY ALA
TGT AAC GCC TCC AAA TTC CAC CAG GGG GCA
        1321
LEU GLY VAL PHE ALA VAL PRO GLU MET CYS
CTA GGG GTA TTC GCC GTA CCA GAG ATG TGT
        1351
LEU ALA GLY ASP SER ASN THR THR THR MET
CTG GCC GGG GAT AGC AAC ACC ACT ACC ATG
        1381
HIS THR SER TYR GLN ASN ALA ASN PRO GLY
CAC ACC AGC TAT CAA AAT GCC AAT CCT GGC
        1411
GLU LYS GLY GLY THR PHE THR GLY THR PHE
GAG AAA GGA GGC ACT TTC ACG GGT ACG TTC
        1441
THR PRO ASP ASN ASN GLN THR SER PRO ALA
ACT CCT GAC AAC AAC CAG ACA TCA CCT GCC
```

FIG. 5D

```
          1471
ARG ARG PHE CYS PRO VAL ASP TYR LEU LEU
CGC AGG TTC TGC CCG GTG GAT TAC CTC CTT
          1501
GLY ASN GLY THR LEU LEU GLY ASN ALA PHE
GGA AAT GGC ACG TTG TTG GGG AAT GCC TTT
          1531
VAL PHE PRO HIS GLN ILE ILE ASN LEU ARG
GTG TTC CCG CAC CAG ATA ATA AAC CTA CGG
          1561
THR ASN ASN CYS ALA THR LEU VAL LEU PRO
ACC AAC AAC TGT GCT ACA CTG GTA CTC CCT
          1591
TYR VAL ASN SER LEU SER ILE ASP SER MET
TAC GTG AAC TCC CTC TCG ATA GAT AGT ATG
          1621
VAL LYS HIS ASN ASN TRP GLY ILE ALA ILE
GTA AAG CAC AAT AAT TGG GGA ATT GCA ATA
          1651
LEU PRO LEU ALA PRO LEU ASN PHE ALA SER
TTA CCA TTG GCC CCA TTA AAT TTT GCT AGT
          1681
GLU SER SER PRO GLU ILE PRO ILE THR LEU
GAG TCC TCC CCA GAG ATT CCA ATC ACC TTG
          1711
THR ILE ALA PRO MET CYS CYS GLU PHE ASN
ACC ATA GCC CCT ATG TGC TGT GAG TTC AAT
          1741
GLY LEU ARG ASN ILE THR LEU PRO ARG LEU
GGA TTA AGA AAC ATC ACC CTG CCA CGC TTA
            VP3 1771
GLN GLY LEU PRO VAL MET ASN THR PRO GLY
CAG GGC CTG CCG GTC ATG AAC ACC CCT GGT
          1801
SER ASN GLN TYR LEU THR ALA ASP ASN PHE
AGC AAT CAA TAT CTT ACT GCA GAC AAC TTC
```

FIG. 5E

```
        1831
GLN SER PRO CYS ALA LEU PRO GLU PHE ASP
CAG TCA CCG TGT GCG CTG CCT GAA TTT GAT
        1861
VAL THR PRO PRO ILE ASP ILE PRO GLY GLU
GTG ACC CCA CCT ATT GAC ATA CCC GGT GAA
        1891
VAL LYS ASN MET MET GLU LEU ALA GLU ILE
GTA AAG AAC ATG ATG GAA TTG GCA GAA ATC
        1921
ASP THR MET ILE PRO PHE ASP LEU SER ALA
GAC ACC ATG ATT CCC TTT GAC TTA AGT GCC
        1951
THR LYS LYS ASN THR MET GLU MET TYR ARG
ACA AAA AAG AAC ACC ATG GAA ATG TAT AGG
        1981
VAL ARG LEU SER ASP LYS PRO HIS THR ASP
GTT CGG TTA AGT GAC AAA CCA CAT ACA GAC
        2011
ASP PRO ILE LEU CYS LEU SER LEU SER PRO
GAT CCC ATA CTC TGC CTG TCA CTC TCT CCA
        2041
ALA SER ASP PRO ARG LEU SER HIS THR MET
GCT TCA GAT CCT AGG TTG TCA CAT ACT ATG
        2071
LEU GLY GLU ILE LEU ASN TYR TYR THR HIS
CTT GGA GAA ATC CTA AAT TAC TAC ACA CAC
        2101
TRP ALA GLY SER LEU LYS PHE THR PHE LEU
TGG GCA GGA TCC CTG AAG TTC ACG TTT CTG
        2131
PHE CYS GLY SER MET MET ALA THR GLY LYS
TTC TGT GGA TCC ATG ATG GCA ACT GGC AAA
        2161
LEU LEU VAL SER TYR ALA PRO PRO GLY ALA
CTG TTG GTG TCA TAC GCG CCT CCT GGA GCC
```

FIG.5F

```
      2191
ASP PRO PRO LYS LYS ARG LYS GLU ALA MET
GAC CCA CCA AAG AAG CGT AAG GAG GCG ATG
      2221
LEU GLY THR HIS VAL ILE TRP ASP ILE GLY
TTG GGA ACA CAT GTG ATC TGG GAC ATA GGA
      2251
LEU GLN SER SER CYS THR MET VAL VAL PRO
CTG CAG TCC TCA TGT ACT ATG GTA GTG CCA
      2281
TRP ILE SER ASN THR THR TYR ARG GLN THR
TGG ATT AGC AAC ACC ACG TAT CGG CAA ACC
      2311
ILE ASP ASP SER PHE THR GLU GLY GLY TYR
ATA GAT GAT AGT TTC ACC GAA GGC GGA TAC
      2341
ILE SER VAL PHE TYR GLN THR ARG ILE VAL
ATC AGC GTC TTC TAC CAA ACT AGA ATA GTC
      2371
VAL PRO LEU SER THR PRO ARG GLU MET ASP
GTC CCT CTT TCG ACA CCC AGA GAG ATG GAC
      2401
ILE LEU GLY PHE VAL SER ALA CYS ASN ASP
ATC CTT GGT TTT GTG TCA GCG TGT AAT GAC
      2431
PHE SER VAL ARG LEU LEU ARG ASP THR THR
TTC AGC GTG CGC TTG TTG CGA GAT ACC ACA
      2461                              ┌►VP1
HIS ILE GLU GLN LYS ALA LEU ALA GLN │GLY
CAT ATA GAG CAA AAA GCG CTA GCA CAG │GGG
      2491
LEU GLY GLN MET LEU GLU SER MET ILE ASP
TTA GGT CAG ATG CTT GAA AGC ATG ATT GAC
      2521
ASN THR VAL ARG GLU THR VAL GLY ALA ALA
AAC ACA GTC CGT GAA ACG GTG GGG GCG GCA
```

FIG. 5G

```
      2551
THR SER ARG ASP ALA LEU PRO ASN THR GLU
ACA TCT AGA GAC GCT CTC CCA AAC ACT GAA
      2581
ALA SER GLY PRO THR HIS SER LYS GLU ILE
GCC AGT GGA CCA ACA CAC TCC AAG GAA ATT
      2611
PRO ALA LEU THR ALA VAL GLU THR GLY ALA
CCG GCA CTC ACC GCA GTG GAA ACT GGG GCC
      2641
THR ASN PRO LEU VAL PRO SER ASP THR VAL
ACA AAT CCA CTA GTC CCT TCT GAT ACA GTG
      2671
GLN THR ARG HIS VAL VAL GLN HIS ARG SER
CAA ACC AGA CAT GTT GTA CAA CAT AGG TCA
      2701
ARG SER GLU SER SER ILE GLU SER PHE PHE
AGG TCA GAG TCT AGC ATA GAG TCT TTC TTC
      2731
ALA ARG GLY ALA CYS VAL THR ILE MET THR
GCG CGG GGT GCA TGC GTG ACC ATT ATG ACC
      2761
VAL ASP ASN PRO ALA SER THR THR ASN LYS
GTG GAT AAC CCA GCT TCC ACC ACG AAT AAG
      2791
ASP LYS LEU PHE ALA VAL TRP LYS ILE THR
GAT AAG CTA TTT GCA GTG TGG AAG ATC ACT
      2821
TYR LYS ASP THR VAL GLN LEU ARG ARG LYS
TAT AAA GAT ACT GTC CAG TTA CGG AGG AAA
      2851
LEU GLU PHE PHE THR TYR SER ARG PHE ASP
TTG GAG TTC TTC ACC TAT TCT AGA TTT GAT
      2881
MET GLU LEU THR PHE VAL VAL THR ALA ASN
ATG GAA CTT ACC TTT GTG GTT ACT GCA AAT
```

FIG.5H

```
      2911
PHE THR GLU THR ASN ASN GLY HIS ALA LEU
TTC ACT GAG ACT AAC AAT GGG CAT GCC TTA
      2941
ASN GLN VAL TYR GLN ILE MET TYR VAL PRO
AAT CAA GTG TAC CAA ATT ATG TAC GTA CCA
      2971
PRO GLY ALA PRO VAL PRO GLU LYS TRP ASP
CCA GGC GCT CCA GTG CCC GAG AAA TGG GAC
      3001
ASP TYR THR TRP GLN THR SER SER ASN PRO
GAC TAC ACA TGG CAA ACC TCA TCA AAT CCA
      3031
SER ILE PHE TYR THR TYR GLY THR ALA PRO
TCA ATC TTT TAC ACC TAC GGA ACA GCT CCA
      3061
ALA ARG ILE SER VAL PRO TYR VAL GLY ILE
GCC CGG ATC TCG GTA CCG TAT GTT GGT ATT
      3091
SER ASN ALA TYR SER HIS PHE TYR ASP GLY
TCG AAC GCC TAT TCA CAC TTT TAC GAC GGT
      3121
PHE SER LYS VAL PRO LEU LYS ASP GLN SER
TTT TCC AAA GTA CCA CTG AAG GAC CAG TCG
      3151
ALA ALA LEU GLY ASP SER LEU TYR GLY ALA
GCA GCA CTA GGT GAC TCC CTT TAT GGT GCA
      3181
ALA SER LEU ASN ASP PHE GLY ILE LEU ALA
GCA TCT CTA AAT GAC TTC GGT ATT TTG GCT
      3211
VAL ARG VAL VAL ASN ASP HIS ASN PRO THR
GTT AGA GTA GTC AAT GAT CAC AAC CCG ACC
      3241
LYS VAL THR SER LYS ILE ARG VAL TYR LEU
AAG GTC ACC TCC AAA ATC AGA GTG TAT CTA
```

FIG. 51

```
            3271
LYS PRO LYS HIS ILE ARG VAL TRP CYS PRO
AAA CCC AAA CAC ATC AGA GTC TGG TGC CCG
            3301
ARG PRO PRO ARG ALA VAL ALA TYR TYR GLY
CGT CCA CCG AGG GCA GTG GCG TAC TAC GGC
            3331
PRO GLY VAL ASP TYR LYS ASP GLY THR LEU
CCT GGA GTG GAT TAC AAG GAT GGT ACG CTT
            3361
THR PRO LEU SER THR LYS ASP LEU THR THR
ACA CCC CTC TCC ACC AAG GAT CTG ACC ACA
          ▶3b 3391
TYR GLY PHE GLY HIS GLN ASN LYS ALA VAL
TAT GGA TTC GGA CAC CAA AAC AAA GCG GTG
            3421
TYR THR ALA GLY TYR LYS ILE CYS ASN TYR
TAC ACT GCA GGT TAC AAA ATT TGC AAC TAC
            3451
HIS LEU ALA THR GLN ASP ASP LEU GLN ASN
CAC TTG GCC ACT CAG GAT GAT TTG CAA AAC
            3481
ALA VAL ASN VAL MET TRP SER ARG ASP LEU
GCA GTG AAC GTC ATG TGG AGT AGA GAC CTC
            3511
LEU VAL THR GLU SER ARG ALA GLN GLY THR
TTA GTC ACA GAA TCA AGA GCC CAG GGC ACC
            3541
ASP SER ILE ALA ARG CYS ASN CYS ASN ALA
GAT TCA ATC GCA AGG TGC AAT TGC AAC GCA
            3571
GLY VAL TYR TYR CYS GLU SER ARG ARG LYS
GGG GTG TAC TAC TGC GAG TCT AGA AGG AAA
            3601
TYR TYR PRO VAL SER PHE VAL GLY PRO THR
TAC TAC CCA GTA TCC TTC GTT GGC CCA ACG
```

FIG.5J

```
      3631
PHE GLN TYR MET GLU ALA ASN ASN TYR TYR
TTC CAG TAC ATG GAG GCT AAT AAC TAT TAC
      3661
PRO ALA ARG TYR GLN SER HIS MET LEU ILE
CCA GCT AGG TAC CAG TCC CAT ATG CTC ATT
      3691
GLY HIS GLY PHE ALA SER PRO GLY ASP CYS
GGC CAT GGA TTC GCA TCT CCA GGG GAT TGT
      3721
GLY GLY ILE LEU ARG CYS HIS HIS GLY VAL
GGT GGC ATA CTC AGA TGT CAC CAC GGG GTG
      3751
ILE GLY ILE ILE THR ALA GLY GLY GLU GLY
ATA GGG ATC ATT ACT GCT GGT GGC GAA GGG
      3781
LEU VAL ALA PHE SER ASP ILE ARG ASP LEU
TTG GTT GCA TTT TCA GAC ATT AGA GAC TTG
      3811
TYR ALA TYR GLU GLU GLU ALA MET GLU GLN
TAT GCC TAC GAA GAA GAA GCC ATG GAA CAA
  →5b   3841
GLY ILE THR ASN TYR ILE GLU SER LEU GLY
GGC ATC ACC AAT TAC ATA GAG TCA CTT GGG
      3871
ALA ALA PHE GLY SER GLY PHE THR GLN GLN
GCC GCA TTT GGA AGT GGA TTT ACT CAG CAG
      3901
ILE SER ASP LYS ILE THR GLU LEU THR ASN
ATT AGC GAC AAA ATA ACA GAG TTG ACC AAT
      3931
MET VAL THR SER THR ILE THR GLU LYS LEU
ATG GTG ACC AGT ACC ATC ACT GAA AAG CTA
      3961
LEU LYS ASN LEU ILE LYS ILE ILE SER SER
CTT AAG AAC TTG ATC AAG ATC ATA TCC TCA
```

FIG. 5K

```
       3991
LEU VAL ILE ILE THR ARG ASN TYR GLU ASP
CTA GTT ATT ATA ACT AGG AAC TAT GAA GAC
       4021
THR THR THR VAL LEU ALA THR LEU ALA LEU
ACC ACA ACA GTG CTC GCT ACC CTG GCC CTT
       4051
LEU GLY CYS ASP ALA SER PRO TRP GLN TRP
CTT GGG TGT GAT GCT TCA CCA TGG CAG TGG
       4081
LEU ARG LYS LYS ALA CYS ASP VAL LEU GLU
CTT AGA AAG AAA GCA TGC GAT GTT CTG GAG
       4111                      →X
ILE PRO TYR VAL ILE LYS GLN│GLY ASP SER
ATA CCT TAT GTC ATC AAG CAA│GGT GAC AGT
       4141
TRP LEU LYS LYS PHE THR GLU ALA CYS ASN
TGG TTG AAG AAG TTT ACT GAA GCA TGC AAC
       4171
ALA ALA LYS GLY LEU GLU TRP VAL SER ASN
GCA GCT AAG GGA CTG GAG TGG GTG TCA AAC
       4201
LYS ILE SER LYS PHE ILE ASP TRP LEU LYS
AAA ATC TCA AAA TTC ATT GAT TGG CTC AAG
       4231
GLU LYS ILE ILE PRO GLN ALA ARG ASP LYS
GAG AAA ATT ATC CCA CAA GCT AGA GAT AAG
       4261
LEU GLU PHE VAL THR LYS LEU ARG GLN LEU
TTG GAA TTT GTA ACA AAA CTT AGA CAA CTA
       4291
GLU MET LEU GLU ASN GLN ILE SER THR ILE
GAA ATG CTG GAA AAC CAA ATC TCA ACT ATA
       4321
HIS GLN SER CYS PRO SER GLN GLU HIS GLN
CAC CAA TCA TGC CCT AGT CAG GAA CAC CAG
```

FIG.5L

```
      4351
GLU ILE LEU PHE ASN ASN VAL ARG TRP LEU
GAA ATT CTA TTC AAT AAT GTC AGA TGG TTA
      4381
SER ILE GLN SER LYS ARG PHE ALA PRO LEU
TCC ATC CAG TCT AAG AGG TTT GCC CCT CTT
      4411
TYR ALA VAL GLU ALA LYS ARG ILE GLN LYS
TAC GCA GTG GAA GCC AAA AGA ATA CAG AAA
      4441
LEU GLU HIS THR ILE ASN ASN TYR ILE GLN
CTA GAG CAT ACT ATT AAC AAC TAC ATA CAG
      4471
PHE LYS SER LYS HIS ARG ILE GLU PRO VAL
TTC AAG AGC AAA CAC CGT ATT GAA CCA GTA
      4501
CYS LEU LEU VAL HIS GLY SER PRO GLY THR
TGT TTG CTA GTA CAT GGC AGC CCC GGA ACA
      4531
GLY LYS SER VAL ALA THR ASN LEU ILE ALA
GGT AAA TCT GTA GCA ACC AAC CTG ATT GCT
      4561
ARG ALA ILE ALA GLU ARG GLU ASN THR SER
AGA GCC ATA GCT GAA AGA GAA AAC ACG TCC
      4591
THR TYR SER LEU PRO PRO ASP PRO SER HIS
ACG TAC TCG CTA CCC CCG GAT CCA TCA CAC
      4621
PHE ASP GLY TYR LYS GLN GLN GLY VAL VAL
TTC GAC GGA TAC AAA CAA CAG GGA GTG GTG
      4651
ILE MET ASP ASP LEU ASN GLN ASN PRO ASP
ATT ATG GAC GAC CTG AAT CAA AAC CCA GAT
      4681
GLY ALA ASP MET LYS LEU PHE CYS GLN MET
GGT GCG GAC ATG AAG CTG TTC TGT CAG ATG
```

FIG.5M

```
        4711
VAL SER THR VAL GLU PHE ILE PRO PRO MET
GTA TCA ACA GTG GAG TTT ATA CCA CCC ATG
        4741
ALA SER LEU GLU GLU LYS GLY ILE LEU PHE
GCA TCC CTG GAG GAG AAA GGA ATC CTG TTT
        4771
THR SER ASN TYR VAL LEU ALA SER THR ASN
ACT TCA AAT TAC GTT CTA GCA TCC ACA AAC
        4801
SER SER ARG ILE SER PRO PRO THR VAL ALA
TCA AGC AGA ATT TCC CCC CCC ACT GTG GCA
        4831
HIS SER ASP ALA LEU ALA ARG ARG PHE ALA
CAC AGT GAT GCA TTA GCC AGG CGC TTT GCG
        4861
PHE ASP MET ASP ILE GLN VAL MET ASN GLU
TTC GAC ATG GAC ATT CAG GTC ATG AAT GAG
        4891
TYR SER ARG ASP GLY LYS LEU ASN MET ALA
TAT TCT AGA GAT GGG AAA TTG AAC ATG GCC
        4921
MET ALA THR GLU MET CYS LYS ASN CYS HIS
ATG GCT ACT GAA ATG TGT AAG AAC TGT CAC
        4951
GLN PRO ALA ASN PHE LYS ARG CYS CYS PRO
CAA CCA GCA AAC TTT AAG AGA TGC TGT CCT
        4981
LEU VAL CYS GLY LYS ALA ILE GLN LEU MET
TTA GTG TGT GGT AAG GCA ATT CAA TTA ATG
        5011
ASP LYS SER SER ARG VAL ARG TYR SER ILE
GAC AAA TCT TCC AGA GTT AGA TAC AGT ATT
        5041
ASP GLN ILE THR THR MET ILE ILE ASN GLU
GAC CAG ATC ACT ACA ATG ATT ATC AAT GAG
```

FIG. 5N

```
       5071
ARG ASN ARG ARG SER ASN ILE GLY ASN CYS
AGA AAC AGA AGA TCC AAC ATT GGC AAT TGT
       5101                  ┌→1b
MET GLU ALA LEU PHE GLN │GLY PRO LEU GLN
ATG GAG GCT TTG TTT CAA │GGA CCA CTC CAG
       5131
TYR LYS ASP LEU LYS ILE ASP ILE LYS THR
TAT AAA GAC TTG AAA ATT GAC ATC AAG ACG
       5161
SER PRO PRO PRO GLU CYS ILE ASN ASP LEU
AGT CCC CCT CCT GAA TGT ATC AAT GAC TTG
       5191
LEU GLN ALA VAL ASP SER GLN GLU VAL ARG
CTC CAA GCA GTT GAC TCC CAG GAG GTG AGA
       5221
ASP TYR CYS GLU LYS LYS GLY TRP ILE VAL
GAT TAC TGT GAG AAG AAG GGT TGG ATA GTC
       5251
ASN ILE THR SER GLN VAL GLN THR GLU ARG
AAC ATC ACC AGC CAG GTT CAA ACA GAA AGG
       5281
ASN ILE ASN ARG ALA MET THR ILE LEU GLN
AAC ATC AAC AGG GCA ATG ACA ATT CTA CAA
       5311
ALA VAL THR THR PHE ALA ALA VAL ALA GLY
GCG GTG ACA ACC TTC GCC GCA GTG GCT GGA
       5341
VAL VAL TYR VAL MET TYR LYS LEU PHE ALA
GTT GTC TAT GTC ATG TAT AAA CTG TTT GCT
       5371  ┌→VPg
GLY HIS GLN │GLY ALA TYR THR GLY LEU PRO
GGA CAC CAG │GGA GCA TAC ACT GGT TTA CCA
       5401
ASN LYS LYS PRO ASN VAL PRO THR ILE ARG
AAC AAA AAA CCC AAC GTG CCC ACC ATT CGG
```

FIG.50

```
         5431           ┌→2
THR ALA LYS VAL GLN │GLY PRO GLY PHE ASP
ACA GCA AAG GTA CAA │GGA CCA GGG TTC GAT
         5461
TYR ALA VAL ALA MET ALA LYS ARG ASN ILE
TAC GCA GTG GCT ATG GCT AAA AGA AAC ATT
         5491
VAL THR ALA THR THR SER LYS GLY GLU PHE
GTT ACA GCA ACT ACT AGC AAG GGA GAG TTC
         5521
THR MET LEU GLY VAL HIS ASP ASN VAL ALA
ACT ATG TTA GGA GTC CAC GAC AAC GTG GCT
         5551
ILE LEU PRO THR HIS ALA SER PRO GLY GLU
ATT TTA CCA ACC CAC GCT TCA CCT GGT GAA
         5581
SER ILE VAL ILE ASP GLY LYS GLU VAL GLU
AGC ATT GTG ATC GAT GGC AAA GAA GTG GAG
         5611
ILE LEU ASP ALA LYS ALA LEU GLU ASP GLN
ATC TTG GAT GCC AAA GCG CTC GAA GAT CAA
         5641
ALA GLY THR ASN LEU GLU ILE THR ILE ILE
GCA GGA ACC AAT CTT GAA ATC ACT ATA ATC
         5671
THR LEU LYS ARG ASN GLU LYS PHE ARG ASP
ACT CTA AAG AGA AAT GAA AAG TTC AGA GAC
         5701
ILE ARG PRO HIS ILE PRO THR GLN ILE THR
ATT AGA CCA CAT ATA CCT ACT CAA ATC ACT
         5731
GLU THR ASN ASP GLY VAL LEU ILE VAL ASN
GAG ACA AAT GAT GGA GTC TTG ATC GTG AAC
         5761
THR SER LYS TYR PRO ASN MET TYR VAL PRO
ACT AGC AAG TAC CCC AAT ATG TAT GTT CCT
```

FIG.5P

```
       5791
VAL GLY ALA VAL THR GLU GLN GLY TYR LEU
GTC GGT GCT GTG ACT GAA CAG GGA TAT CTA
       5821
ASN LEU GLY GLY ARG GLN THR ALA ARG THR
AAT CTC GGT GGG CGC CAA ACT GCT CGT ACT
       5851
LEU MET TYR ASN PHE PRO THR ARG ALA GLY
CTA ATG TAC AAC TTT CCA ACC AGA GCA GGA
       5881
GLN CYS GLY GLY VAL ILE THR CYS THR GLY
CAG TGT GGT GGA GTC ATC ACA TGT ACT GGG
       5911
LYS VAL ILE GLY MET HIS VAL GLY GLY ASN
AAA GTC ATC GGG ATG CAT GTT GGT GGG AAC
       5941
GLY SER HIS GLY PHE ALA ALA ALA LEU LYS
GGT TCA CAC GGG TTT GCA GCG GCC CTG AAG
       5971                          →4(p63)
ARG SER TYR PHE THR GLN SER GLN GLY GLU
CGA TCA TAC TTC ACT CAG AGT CAA GGT GAA
       6001
ILE GLN TRP MET ARG PRO SER LYS GLU VAL
ATC CAG TGG ATG AGA CCT TCG AAG GAA GTG
       6031
GLY TYR PRO ILE ILE ASN ALA PRO SER LYS
GGA TAT CCA ATC ATA AAT GCC CCG TCC AAA
       6061
THR LYS LEU GLU PRO SER ALA PHE HIS TYR
ACC AAG CTT GAA CCC AGT GCT TTC CAC TAT
       6091
VAL PHE GLU GLY VAL LYS GLU PRO ALA VAL
GTG TTT GAA GGG GTG AAG GAA CCA GCA GTC
       6121
LEU THR LYS ASN ASP PRO ARG LEU LYS THR
CTC ACT AAA AAC GAT CCC AGG CTT AAG ACA
```

FIG.5Q

```
          6151
ASP PHE GLU GLU ALA ILE PHE SER LYS TYR
GAC TTT GAG GAG GCA ATT TTC TCC AAG TAC
          6181
VAL GLY ASN LYS ILE THR GLU VAL ASP GLU
GTG GGT AAC AAA ATT ACT GAA GTG GAT GAG
          6211
TYR MET LYS GLU ALA VAL ASP HIS TYR ALA
TAC ATG AAA GAG GCA GTA GAC CAC TAT GCT
          6241
GLY GLN LEU MET SER LEU ASP ILE ASN THR
GGC CAG CTC ATG TCA CTA GAC ATC AAC ACA
          6271
GLU GLN MET CYS LEU GLU ASP ALA MET TYR
GAA CAA ATG TGC TTG GAG GAT GCC ATG TAT
          6301
GLY THR ASP GLY LEU GLU ALA LEU ASP LEU
GGC ACT GAT GGT CTA GAA GCA CTT GAT TTG
          6331
SER THR SER ALA GLY TYR PRO TYR VAL ALA
TCC ACC AGT GCT GGC TAC CCT TAT GTA GCA
          6361
MET GLY LYS LYS LYS ARG ASP ILE LEU ASN
ATG GGA AAG AAG AAG AGA GAC ATC TTG AAC
          6391
LYS GLN THR ARG ASP THR LYS GLU MET GLN
AAA CAA ACC AGA GAC ACT AAG GAA ATG CAA
          6421
LYS LEU LEU ASP THR TYR GLY ILE ASN LEU
AAA CTG CTC GAC ACA TAT GGA ATC AAC CTC
          6451
PRO LEU VAL THR TYR VAL LYS ASP GLU LEU
CCA CTG GTG ACT TAT GTA AAG GAT GAA CTT
          6481
ARG SER LYS THR LYS VAL GLU GLN GLY LYS
AGA TCC AAA ACA AAG GTT GAG CAG GGG AAA
```

FIG.5R

```
            6511
SER ARG LEU ILE GLU ALA SER SER LEU ASN
TCC AGA TTA ATT GAA GCT TCT AGT TTG AAT
            6541
ASP SER VAL ALA MET ARG MET ALA PHE GLY
GAC TCA GTG GCA ATG AGA ATG GCT TTT GGG
            6571
ASN LEU TYR ALA ALA PHE HIS LYS ASN PRO
AAC CTA TAT GCT GCT TTT CAC AAA AAC CCA
            6601
GLY VAL ILE THR GLY SER ALA VAL GLY CYS
GGA GTG ATA ACA GGT TCA GCA GTG GGG TGC
            6631
ASP PRO ASP LEU PHE TRP SER LYS ILE PRO
GAT CCA GAT TTG TTT TGG AGC AAA ATT CCG
            6661
VAL LEU MET GLU GLU LYS LEU PHE ALA PHE
GTA TTG ATG GAA GAG AAG CTG TTT GCT TTT
            6691
ASP TYR THR GLY TYR ASP ALA SER LEU SER
GAC TAC ACA GGG TAT GAT GCA TCT CTC AGC
            6721
PRO ALA TRP PHE GLU ALA LEU LYS MET VAL
CCT GCT TGG TTC GAG GCA CTA AAG ATG GTG
            6751
LEU GLU LYS ILE GLY PHE GLY ASP ARG VAL
CTT GAG AAA ATC GGA TTC GGA GAC AGA GTT
            6781
ASP TYR ILE ASP TYR LEU ASN HIS SER HIS
GAC TAC ATC GAC TAC CTA AAC CAC TCA CAC
            6811
HIS LEU TYR LYS ASN LYS THR TYR CYS VAL
CAC CTG TAC AAG AAT AAA ACA TAC TGT GTC
            6841
LYS GLY GLY MET PRO SER GLY CYS SER GLY
AAG GGC GGT ATG CCA TCT GGC TGC TCA GGC
```

FIG.5S

```
      6871
THR SER ILE PHE ASN SER MET ILE ASN ASN
ACT TCA ATT TTT AAC TCA ATG ATT AAC AAC
      6901
LEU ILE ILE ARG THR LEU LEU LEU LYS THR
TTG ATT ATC AGG ACA CTC TTA CTG AAA ACC
      6931
TYR LYS GLY ILE ASP LEU ASP HIS LEU LYS
TAC AAG GGC ATA GAT TTA GAC CAC CTA AAA
      6961
MET ILE ALA TYR GLY ASP ASP VAL ILE ALA
ATG ATT GCC TAT GGT GAT GAT GTA ATT GCT
      6991
SER TYR PRO HIS GLU VAL ASP ALA SER LEU
TCC TAC CCC CAT GAA GTT GAC GCT AGT CTC
      7021
LEU ALA GLN SER GLY LYS ASP TYR GLY LEU
CTA GCC CAA TCA GGA AAA GAC TAT GGA CTA
      7051
THR MET THR PRO ALA ASP LYS SER ALA THR
ACT ATG ACT CCA GCT GAC AAA TCA GCT ACA
      7081
PHE GLU THR VAL THR TRP GLU ASN VAL THR
TTT GAA ACA GTC ACA TGG GAG AAT GTA ACA
      7111
PHE LEU LYS ARG PHE PHE ARG ALA ASP GLU
TTC TTG AAG AGA TTC TTC AGG GCA GAC GAG
      7141
LYS TYR PRO PHE LEU ILE HIS PRO VAL MET
AAA TAC CCA TTT CTT ATT CAT CCA GTA ATG
      7171
PRO MET LYS GLU ILE HIS GLU SER ILE ARG
CCA ATG AAG GAA ATT CAT GAA TCA ATT AGA
      7201
TRP THR LYS ASP PRO ARG ASN THR GLN ASP
TGG ACT AAA GAT CCT AGG AAC ACT CAG GAT
```

FIG.5T

```
        7231
HIS VAL ARG SER LEU CYS LEU LEU ALA TRP
CAC GTT CGC TCT CTG TGC CTT TTA GCT TGG
        7261
HIS ASN GLY GLU GLU GLU TYR ASN LYS PHE
CAC AAT GGC GAA GAA GAA TAT AAC AAA TTC
        7291
LEU ALA LYS ILE ARG SER VAL PRO ILE GLY
CTA GCT AAA ATC AGG AGT GTG CCA ATT GGA
        7321
ARG ALA LEU LEU LEU PRO GLU TYR SER THR
AGA GCT TTA TTG CTC CCA GAG TAC TCA ACA
        7351
LEU TYR ARG ARG TRP LEU ASP SER PHE END
TTG TAC CGC CGT TGG CTT GAC TCA TTT TAG
END     7382
TAA CCCTACCTCAGTCGAATTGGATTGGGTCATACTGT
        7421
TGTAGGGGTAAATTTTTCTTTAATTCGGAG--POLY(A)
```

PRODUCTION OF COMPLEMENTARY DNA REPRESENTING RNA VIRAL SEQUENCES BY RECOMBINANT DNA METHODS AND USES THEREFOR

GOVERNMENT SUPPORT

The work described herein was supported by one or more grants from the National Institutes of Health.

RELATED APPLICATIONS

This is a continuation-in-part application of Ser. No. 255,879, filed Apr. 20, 1981, now abandoned.

TECHNICAL FIELD

This invention is in the field of microbiology and more specifically relates to recombinant DNA techniques for producing genetically-engineered microorganisms.

BACKGROUND ART

Poliovirus, one of the human picornaviruses, has been extensively studied because it is the causative agent for serious human disease. Because of these studies, it is known that the virion of poliovirus consists of a small icosahedron, 25-30 nm in diameter, composed entirely of four polypeptides, which are designated VP1, VP2, VP3 and VP4. A single strand of infectious positive-stranded RNA of molecular weight $2.7 \times 10^6$ daltons is enclosed within this protein coat. This size is equivalent to approximately 7500 bases, which can code for about 2500 amino acids.

Despite the extensive studies made of poliovirus, there still remain many problems with the current techniques available for the study, detection and production of this virus, as well as with the techniques used to produce antibodies against poliovirus. For example, the need for improvements in techniques for detection can be seen when it is recognized that poliovirus RNA cannot be practically employed in the detection of poliovirus. This is because poliovirus RNA is in short supply, is unstable, and does not normally bind to other poliovirus RNA.

To date, the major assay for detecting the presence of poliovirus is a biological technique in which samples are analyzed by a plaque assay employing human cell lines to detect the presence of virus. See Dulbecco, R. and Vogt, M., *J. Exptl. Med.* 99, 167 (1954). This procedure is relatively time consuming and expensive.

Other RNA viruses, many of which have not been as extensively studied as poliovirus, present analogous or even worse problems than poliovirus, in their study, detection, production or use in preparing vaccines or antibodies.

DISCLOSURE OF THE INVENTION

This invention relates to the production of complementary DNA representing RNA viral sequences (RNA viral cDNA) and to methods for using such RNA viral cDNA.

In one embodiment, RNA viral cDNA is produced by reverse transcribing viral RNA and inserting the resulting cDNA molecule into a recombinant DNA vector. Appropriate cells are then transformed with the recombinant DNA vector, cloned and grown under conditions sufficient for production of RNA viral cDNA. This cDNA can then be harvested from the clonal cell culture and used, as is, or further modified for certain applications.

In a particular embodiment, bacteria are modified by genetic engineering techniques to make such bacteria capable of producing poliovirus double-stranded complementary DNA (ds cDNA). In this method, poliovirus singlestranded (ss) RNA is reverse transcribed to provide poliovirus ss cDNA which is extended to ds cDNA and then inserted into a bacterial plasmid to create a chimeric plasmid. The chimeric plasmid containing the ds cDNA is then inserted into bacterial cells by transforming the bacterial cells with the chimeric plasmid. Bacterial cells which have been so transformed can then be cloned and clonal cell lines grown in cell culture to replicate the chimeric plasmid. The poliovirus ds cDNA can then be recovered by enzymatically cleaving it from replicated chimeric plasmids.

This method provides for the microbiological production of relatively large quantities of RNA viral cDNA at reasonable costs. The cDNA, in turn, can be employed in assays for the detection of RNA viruses, such as poliovirus, since the RNA viral cDNA will bind specifically to RNA virus. Such assays can be performed quickly and easily and they offer the potential for being extremely sensitive for RNA virus detection.

RNA viral cDNA can also be employed in the production of either more RNA viral antigen or antibodies to such an antigen. In these methods, cDNA to viral RNA is produced, as described above. For antigen production, cDNA capable of stimulating antigen production is selected and inserted into cells capable of producing the antigen after which the cells are cultured under conditions suitable for antigen production, and antigen is then harvested. For antibody production, harvested antigen is employed to immunize a host capable of producing antibodies to the original virus employed. Monoclonal antibodies can be produced employing antibody-producing cells from the host and known techniques, such as the formation of hybridoma cell lines.

Surprisingly, it has been found that a full-length poliovirus cDNA molecule produced by the methods described herein and transfected into cells is itself infectious. Such infectious cDNA molecules offer great potential in the production of viral antigens, antibodies and vaccines over their counterpart RNA molecules. For example, a cDNA molecule can be mutagenized with known recombinant DNA techniques. The mutagenized cDNA can be transfected into cultured cells and the resulting viral particles will contain the desired alteration. Such RNA viral particles may offer distinct advantages over their wild-type counterparts in the production of vaccines.

FIG. 5 sets forth the complete nucleotide sequence of the poliovirus cDNA insert in clone pVR106.

BEST MODE FOR CARRYING OUT THE INVENTION

As used herein, the terms "poliovirus RNA," "poliovirus cDNA," "picornavirus RNA," "picornavirus cDNA," "viral RNA," etc., mean the whole RNA or DNA molecule or any significant portion thereof. Thus, the term "poliovirus cDNA" is used to mean DNA complementary to the entire poliovirus RNA or DNA complementary to any significant portion of the poliovirus RNA molecule.

The methods described herein for producing RNA viral CDNA employ fundamental gene splicing techniques which have been described in the scientific literature. For example, U.S. Pat. No. 4,227,224, issued to Stanley N. Cohen and Herbert W. Boyer, on Dec. 2, 1980, describes many of these techniques. The teachings of the Cohen and Boyer patent, therefore, are incorporated herein by reference.

Figure 1:
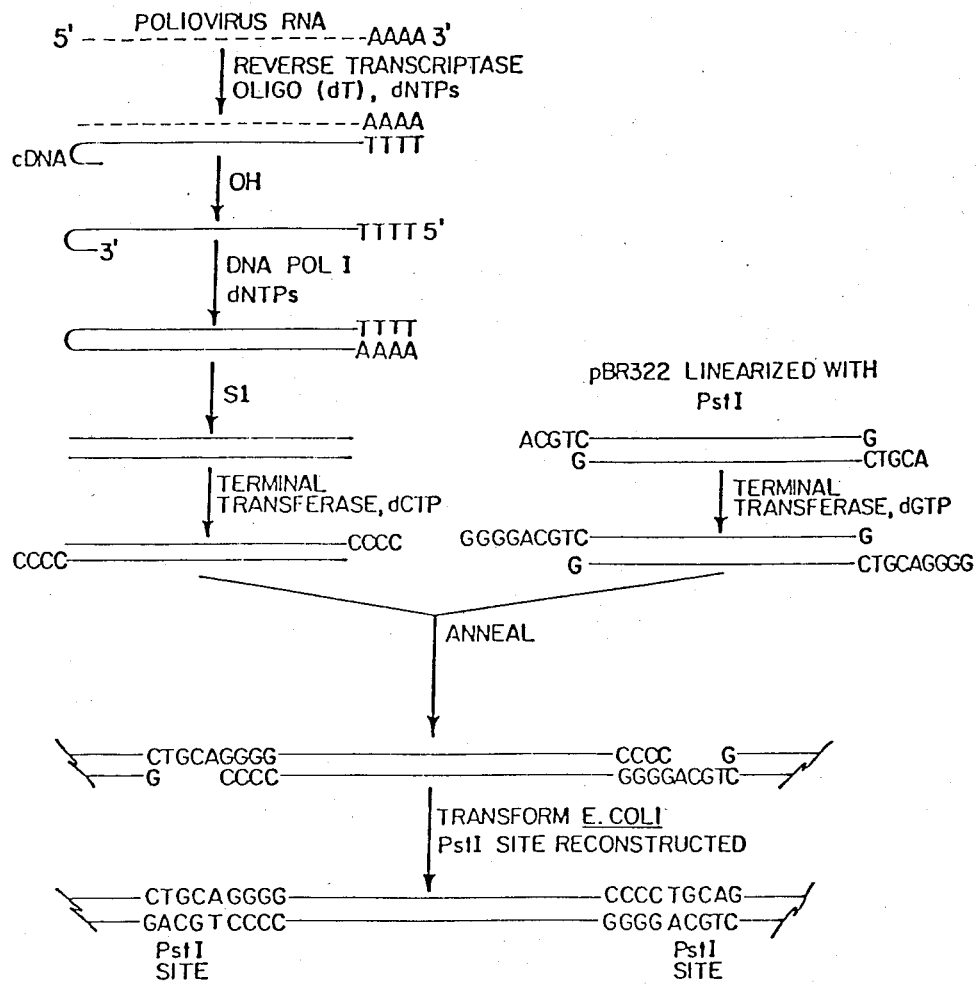
FIG. 1 is a schematic diagram illustrating the production of a bacterial chimeric plasmid containing poliovirus ds cDNA.

A more specific description of the techniques which can be employed in producing poliovirus ds cDNA will now be presented in conjunction with FIG. 1, a schematic diagram illustrating these techniques.

Type 1 poliovirus is employed. Such virus can be obtained by growing epithelioid cells in suspension culture and infecting the culture with poliovirus, Type 1. The infected cells are then lysed with detergent to release virus particles, which are purified by centrifugation.

Poliovirus ss RNA can be extracted from the purified viral particles by phenol-chloroform extraction. The extracted ss RNA is then precipitated by ethanol precipitation.

The poliovirus ss RNA is then employed in the synthesis of poliovirus ds cDNA, as illustrated. Initially, the poliovirus ss RNA is reverse transcribed employing the enzyme reverse transcriptase, also known as RNA-dependent DNA polymerase. See Kacian, D. L. and Myers, J. C. (1976) *PNAS* 73:2191–5. Typically, Tris-HCl buffer, pH 8.3, magnesium ions (Mg++), dithiothreitol, the fourdeoxynucloeside triphosphates (dATP, dCTP, dGTP and TTP), and at least one labeled deoxynucleoside triphosphate for monitoring the product are added to the reaction mixture. Oligo(dT) is also added as a primer which hybridizes to the poly(A) end of poliovirus RNA thereby providing a site for initiation of reverse transcription. The reaction mixture is incubated under conditions to allow the enzyme to synthesize a complementary ss DNA copy of the poliovirus genome starting from the 3' poly(A) end and continuing to the 5' end of the genome. The reaction can be halted by the addition of ethylene diamine tetraacetic acid (EDTA).

The RNA template is then removed with alkali and the ss cDNA molecules are fractionated on a sucrose density gradient. Larger molecules are typically kept. These larger molecules are then placed in another reaction mixture containing Tris-HCl buffer, pH 7.5, Mg++, dithiothreitol, the 4-deoxynucleoside triphosphates, and the Klenow 1 fragment of DNA polymerase I. This reaction mixture is maintained under conditions sufficient to allow the DNA polymerase I to extend the cDNA molecule initiating synthesis at the snap-back formed at the 3' end of the molecule. In a typical example, the reaction mixture might be incubated at 37° for about 30 minutes, which is usually sufficient for formation of the second complementary DNA strand, as illustrated. See Humphries et al. (1978), *Nucleic Acids Res.*, 5:905–24.

S1 nuclease is then employed to cleave the loop at one end of the molecule. See Bhat and Piatigorsky (1975), *PNAS*, 76:3299–3303.

The ds cDNA can then be tailed with oligo(dC) at the 3' ends by employing terminal transferase and dCTP. See Boyer et al. (1977) in "Recombinant Molecules: Impact on Science and Society" (R. F. Beers and E. G. Bassett, eds.) pp 9–20, Raven, N. Y. The tailed ds DNA can be electrophoresed on an agarose gel, and the largest fragments are then eluted from gel slices by electrophoresis. This leaves ds cDNA having poly(C) at both ends to serve as "sticky" ends in subsequent binding to a cleaved bacterial plasmid in order to form a recombinant DNA molecule.

Plasmid pBR322 can be employed to illustrate chimeric plasmid formation. Plasmid pBR322 is a well characterized plasmid known to contain selectable markers. This plasmid contains one gene coding for tetracycline resistance as well as a gene coding for ampicillin resistance. Since the poliovirus ds cDNA sequences are inserted into the gene for ampicillin resistance, successfully transformed bacterial cells are ampicillin sensitive ($Amp^s$) and tetracycline resistant ($Tet^R$), the latter providing a marker for transformed cells.

Plasmid pBR322 is cleaved using the restriction enzyme Pst I at the gene coding for ampicillin resistance. The resulting linearized plasmid is then tailed with oligo(dG) employing the enzyme terminal transferase and dGTP to produce "sticky" ends on the linearized cleaved plasmid chains. These plasmid chains can be purified by phenol extraction.

The oligo(dG) tailed plasmid DNA and the oligo(dC) tailed poliovirus ds cDNA are then hybridized in solution. This can be accomplished by mixing these DNA species in an equimolar ratio in 0.1 M NaCl, heating for 2 minutes at 68° and then incubating at 45° for 3–4 hours. See Boyer et al., 1977.

The hybridized plasmid-poliovirus ds cDNA is then inserted into *E. coli* in order to reconstruct the Pst I site, to amplify the plasmid DNA, and to identify clones which contain recombinant plasmids. See Dagert, M. and Ehrlich, S. D. (1979), *Gene*, 23–28. Once the hybrid molecule is inserted, the single-stranded gap is repaired by the bacteria. This reconstruction provides a Pst I site which the Pst I enzyme can later recognize and cleave to separate the poliovirus ds cDNA sequences from replicated plasmids.

*E. coli* cells transformed with the hybrid molecules can then be selected in the presence of tetracycline and later screened for ampicillin sensitivity. Those clones identified as $Tet^r$ $Amp^s$ can then be analyzed by colony hybridization in order to detect specific poliovirus sequences in isolated clones. See Grunstein and Hogness (1977), *PNAS* 72:3961–5. $Tet^r$ $Amp^s$ clones can be grown on nitrocellulose filters on top of agar medium. Colonies are lysed on the nitrocellulose and the DNA is fixed to the filters. The DNA on the filters is then hybridized with $^{32}P$-labeled poliovirus cDNA in sealed polyethylene bags. Autoradiography of the washed and dried filters reveals which colonies contain specific poliovirus sequences, since the DNA from these colonies will hybridize to the labeled poliovirus cDNA and appear as dark spots when the filters are exposed to X-ray film.

Plasmid DNA from positive clones can be obtained using known techniques. See, for example, Meagher et al. (1977) and Guerry et al. (1973).

The DNA can be subjected to electrophoretic analysis on agarose gels after digestion with Pst I. Comparison of the digestion pattern of pBR322 and the hybrid plasmids obtained from positive clones indicates the length of the inserted DNA.

Those skilled in the art will recognize, of course, that other materials and conditions can be employed other than those specifically described in the aforementioned embodiment. For example, although Type 1 poliovirus was employed, it is believed that either Type 2 or Type 3 could also be employed, if desired. Additionally, it is clear that bacterial cells other than E. coli could be employed. For example, B. subtilis could also be employed as well as many other bacterial strains.

As will be clear to those skilled in the art, the methods described above are not limited to poliovirus and are equally applicable with other RNA viruses. This is particularly true, of course, for RNA viruses having a genome formed from a single positive strand of RNA. These include: picornaviruses other than poliovirus, such as coxsackieviruses, rhinoviruses, and foot and mouth disease viruses; and togaviruses, such as Type A (Alphaviruses) and Type B (Flaviviruses).

Similarly, although bacterial plasmids have been employed in producing poliovirus cDNA sequences, other recombinant DNA vectors could be employed. Examples of other recombinant DNA vectors include phages, animal viruses and yeast vectors. Hosts which allow the recombinant DNA vector to multiply are chosen, of course.

Figure 2:
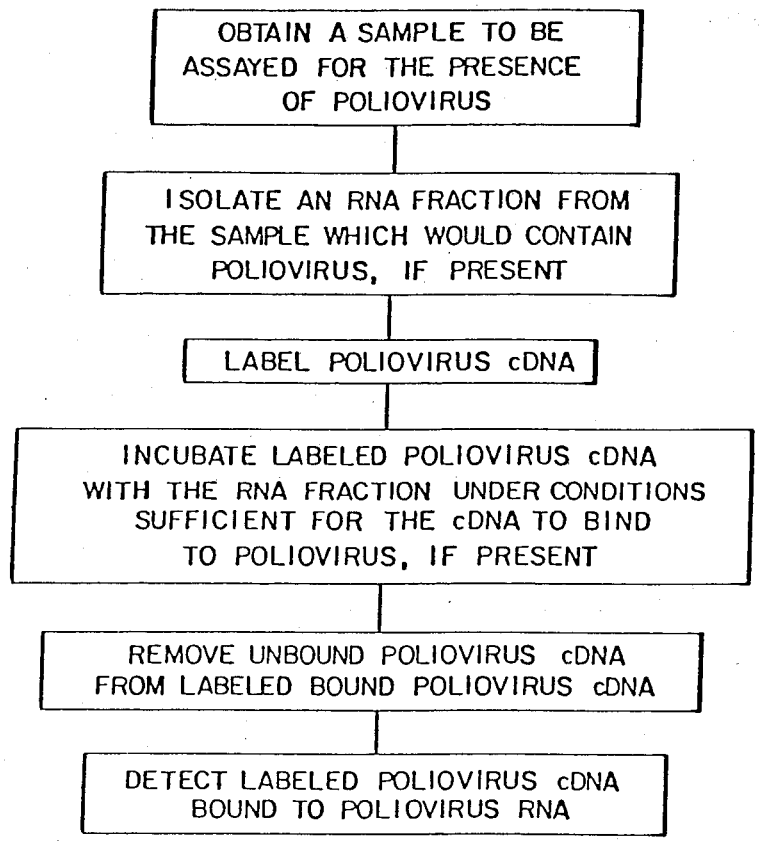
FIG. 2 is a block diagram illustrating one embodiment of an assay employing poliovirus cDNA which could be produced according to the methods described herein.

One significant use for RNA viral cDNA produced according to this invention, such as poliovirus cDNA, is in assays to detect the presence of an RNA virus. In a typical assay for poliovirus, for example, a patient sample, such as cerebrospinal fluid, can be assayed as illustrated in FIG. 2. The RNA fraction of the patient sample is first isolated, which can be done by phenol extraction and ethanol precipitation. This RNA fraction need not be pure, but it must be a fraction which would contain poliovirus RNA if poliovirus were present in the original sample. Poliovirus cDNA is first labeled, e.g., with a radioactive material such as tritium, iodine, or $^{32}P$, and subsequently incubated with the RNA fraction under conditions to allow the labeled poliovirus cDNA to bind to poliovirus RNA, if present. After incubation, unbound labeled poliovirus cDNA is separated and bound labeled cDNA poliovirus is then detected in a scintillation counter or by other means.

Other patient samples, of course, such as blood serum or a biopsy, might be employed. Additionally, the assay can be performed on other liquid samples which might contain poliovirus, such as sewerage. Similarly, the assay can be employed for RNA viruses other than poliovirus.

A solid-phase assay, although not illustrated, might be performed. Additionally, the label need not be a radioactive isotope, but might be an enzyme, optical label, etc.

Another significant use for RNA viral cDNA produced according to this invention is in the production of antibodies against an RNA virus or viral particle.

Antibodies could be produced by reverse transcribing viral RNA to provide cDNA, inserting the cDNA into a recombinant DNA vector and transforming cells in which said recombinant DNA vector can multiply. Transformed cells can then be cloned to produce a cell line capable of replicating the cDNA, the cell line can be cultured under conditions sufficient for the production of cDNA and cDNA can then be harvested from the cell culture. Specific cDNA could be selected and isolated which was capable of directing antigen synthesis in cells and subsequently inserted into cells so that these cells would produce antigen. A host, such as an animal, could then be immunized with the antigen to cause the host to produce antibodies against the original RNA virus or a portion thereof.

Experiments have shown that RNA viral cDNA can be infectious, a surprising finding. These experiments were performed employing full-length, cloned cDNA copies of the RNA genome of poliovirus constructed in the Pst I site of the bacterial plasmid pBR322 (See Examples below). Cultured mammalian cells transfected with these hybrid plasmids produced infectious poliovirus. Cells transfected with a different poliovirus cDNA clone, which lacked the first 115 base pairs of the poliovirus genome, did not produce virus.

This finding means that it is possible to produce RNA virus particles by transfecting cells with cDNA for the RNA virus, culturing the cells under conditions suitable for virus production, and subsequently harvesting the RNA virus particles.

It also means that it will be possible to perform genetic manipulations not possible with RNA which may open up a variety of new approaches to the study of RNA viruses and vaccine production.

For example, a vaccine having properties different from one produced from current vaccine strains could be prepared from cDNA as follows. Initially, a cDNA copy of the RNA genome could be produced as described herein, and the cDNA could be mutagenized employing recombinant DNA techniques. Cells capable of producing RNA viruses could then be transfected with the cDNA and cultured under conditions sufficient to produce the altered virus, which could then be employed in vaccine production.

In one specific approach, specific areas of the viral genome can be deleted from the cDNA using recombinant DNA techniques. Plasmids containing the altered cDNA could then be transfected into cells, such as mammalian cells. Virus particles produced by the cells would be recovered and assayed for attenuation in a suitable host.

Transfection into cells can be achieved by known techniques. For example, the calcium phosphate DNA coprecipitate technique, originally described by Graham and Van der Eb, is suitable. See *Virology* 52, 456 (1973). Similarly, the DNA/DEAE-dextran method, originally described by McCutcheon and Pagano, is also suitable. See *J. Nat'l Cancer Inst.* 41, 351 (1968). Those skilled in the art may know, or will be able to find using no more than routine experimentation, other suitable transfection techniques.

The invention is further and more specifically illustrated by the following examples.

EXAMPLE 1

Preparation of Hybridized Plasmid-Poliovirus ds cDNA and Cloning in *E. Coli*

1. Preparation of Poliovirus RNA

Poliovirus RNA was obtained using standard procedures (Flanegan et al., 1977, *PNAS* 74:961). HeLa cells were grown in suspension culture to a density of $4 \times 10^5$ cells per ml, centrifuged, and infected with a stock of poliovirus type 1 at a multiplicity of infection (MOI) of 10. Infection was allowed to proceed for 6 hours at 37°, at which time the cells were centrifuged. Virus was released from cells with detergent and purified from the cytoplasm by cesium chloride equilibrium centrifugation. RNA was then extracted from virions by phenol-chloroform extraction and ethanol precipitation. (See Flanegan et al., 1977.)

2. Synthesis of Poliovirus Double-Stranded cDNA a. First Strand Synthesis

Poliovirus cDNA was synthesized in a 0.5 ml reaction mixture containing poliovirus RNA (50 µg/ml), 50 mM Tris HCl (pH 8.3), 10 mM $MgCl_2$, 50 mM KCl, 0.4 mM dithiothreitol, 30 µg/ml oligo(deoxythymidylate), 4mM sodium pyrophosphate, 0.5 mM each of dATP, dCTP, dGTP, and dTTP, 100 µCi/ml $\alpha$-$^{32}$P-dCTP and 150 U reverse transcriptase. The mixture was incubated at 42° for 60' and terminated by addition of EDTA. The reaction mixture was phenol extracted and ethanol precipitated, and the pellet was resuspended in 0.2 ml of a buffer containing 0.3 N NaOH, 0.7 M NaCl, 5 mM EDTA. The reaction product was subjected to alkaline sucrose gradient sedimentation at 35,000 rpm in a Beckman SW41 rotor at 20°. Fractions of 0.2 ml were collected from the gradient and analyzed by alkaline agarose gel electrophoresis. Those fractions which contained full-length poliovirus cDNA were pooled, ethanol precipitated and resuspended in 0.05 ml of water.

b. Second Strand Synthesis

Full length poliovirus cDNA (approximately 0.5 µg) was incubated in a reaction mixture containing 10 mM Tris HCl (pH 7.5), 5 mM $MgCl_2$, 5 mM dithiothreitol, and the Klenow fragment of DNA polymerase I (0.003 U/ng cDNA). The mixture was incubated at 37° for 30' and terminated by phenol extraction. The aqueous phase was applied to a $1 \times 10$ cm column of Sephadex G-100 equilibrated with 0.1 M NaCl, 10 mM Tris HCl (pH 7.5), 1 mM EDTA and developed with the same buffer. The void fractions of the column were pooled.

c. $S_1$ Nuclease Treatment

Double-stranded poliovirus cDNA, when prepared as described above, was in a volume of 1.0-1.5 ml. This material was combined with a buffer so that the final concentrations were 0.3 M NaCl, 30 mM NaOAc (pH 4.5), 3 mM $ZnCl_2$, and 5% glycerin. Nuclease $S_1$ was then added to the mixture in an amount previously determined to cleave the loop at one end of the cDNA duplex without nicking the rest of the molecule. The mixture was incubated at 37° for 60 min. The reaction was stopped by phenol extraction, and the aqueous phase was dialyzed against a buffer containing 5 mM Tris HCl (pH 7.5), 0.5 mM EDTA. After dialysis, the cDNA was twice precipitated with ethanol and resuspended in 0.2 ml of water.

d. Addition of Poly(deoxcytidylate) to the Poliovirus ds cDNA

The cDNA from the previous step [0.05-1 µg] was added to a 0.1 ml reaction mixture containing 0.15 M cacodylic acid, 1 mM $CoCl_2$, 0.2 mM dithiothreitol, 50 µg/ml bovine serum albumin and 0.15 mM dCTP. An excess of terminal deoxynucleotidyl transferase [6 U] was added and the reaction was allowed to proceed at room temperature for 20'. At the end of this time, the reaction mixture was phenol extracted, ether extracted twice, and ethanol precipitated. The final pellet was resuspended in 0.05 ml of 0.1 M NaCl, 10 mM Tris HCl (pH 7.5), 1 mM EDTA. The material is referred to as C-tailed poliovirus ds cDNA.

3. Molecular Recombination of Poliovirus ds cDNA a. Preparation of Vector

DNA of the plasmid pBR322 was cleaved with restriction endonuclease Pst I in a 0.1 ml reaction mixture containing DNA [500 µg/ml], 15 mM Tris.HCl (pH 7.5), 5 mM $MgCl_2$, 50 mM NaCl and excess enzyme. The reaction was incubated at 37° for one hour and stopped by phenol extraction. The plasmid DNA was ethanol precipitated and resuspended in 0.02 ml of water.

Poly(deoxyguanylate) was added to the 3' ends of the plasmid DNA by the procedure described in section 2(d), above. The differences were: (1) dGTP was used instead of dCTP; (2) the reaction volume was increased to 0.3 ml, (3) the reaction was allowed to proceed at 20° for 30-60 seconds. After the reaction, the mixture was phenol extracted and chromatographed on a $1 \text{ cm} \times 10$ cm column of Sephadex G-100 in 10 mM NaCl, 1 mM Tris-HCl(pH 7.4), 0.1 mM EDTA. The void fractions were pooled, and concentrated 10-fold under a stream of nitrogen gas. This material is referred to as "G-tailed pBR322 DNA."

b. Annealing of Poliovirus cDNA and Vector Plasmid

An equimolar amount of G-tailed pBR322 DNA and C-tailed poliovirus ds cDNA was mixed in a buffer containing 1 µg/ml G-tailed pBR322 DNA, the appropriate amount of poliovirus cDNA, 0.1 M NaCl, 10 mM Tris.HCl(pH 7.5), 1 mM EDTA. The mixture was heated to 68° for 2' and then placed at 45° for 3-4 hours. After this period, the annealed material was stored at 4° until transformation was performed.

c. Transformation

Cells of the bacterium *E. coli* were made competent for transformation by the following procedure. Cells were grown in 100 ml of L-broth to an optical density at 550 nanometers of 0.1. The cells were centrifuged, resuspended in 20 ml of cold 0.1 M $CaCl_2$ and placed on ice for 25 minutes. After this time, the cells were centrifuged, resuspended in 1.0 ml of cold 0.1 M $CaCl_2$, and held on ice for 24 hours.

Annealed DNA from 3(b) above [0.001 µg] was added to 0.1 ml of competent *E. coli* and incubated on ice for 15'. This mixture was then transferred to 37° for 5 minutes; then 1 ml of L-broth was added and the mixture was shaken for 1 hour at 37°. After this period, 3 ml of soft agar were added and the mixture was poured onto a plate of L-agar containing 15 µg/ml tetracycline. Plates were incubated at 37° until bacterial colonies were visible (usually 18 hours).

d. Identification of Poliovirus-Specific Clones

Bacterial colonies on tetracycline plates were transferred by toothpick to an array on one L-agar plate containing 50 μg/ml ampicillin, and another tetracycline-containing agar plate. Colonies which were identified as ampicillin-sensitive, tetracycline resistant were removed by toothpick to an array on a new tetracycline plate, and allowed to grow 18 hours at 37°. These colonies were then screened for poliovirus DNA using the colony hybridization technique of Grunstein and Hogness, (1975), PNAS 72:3961-5. Briefly, colonies were transferred to nitrocellulose filters, the bacteria were lysed on the filter and the bacterial DNA was fixed onto the nitrocellulose. The filters were then hybridized to an isotopically labeled poliovirus cDNA probe, washed, and autoradiographed. Colonies which retained the radioactive probes were identified as containing poliovirus cDNA sequences.

Many positive clones were examined by isolating plasmid DNA, cleaving with restriction endonuclease Pst I, and determining the size of the poliovirus DNA insert by electrophoresis on agarose gels. Those plasmids containing the longest inserts [4.0 Kbp-6.5 Kbp] were aligned on the viral genome using nucleotode sequence analysis and restriction enzyme mapping techniques.

EXAMPLE 2

Construction Of Nearly Full-Length Poliovirus cDNA Clone

Figure 3:
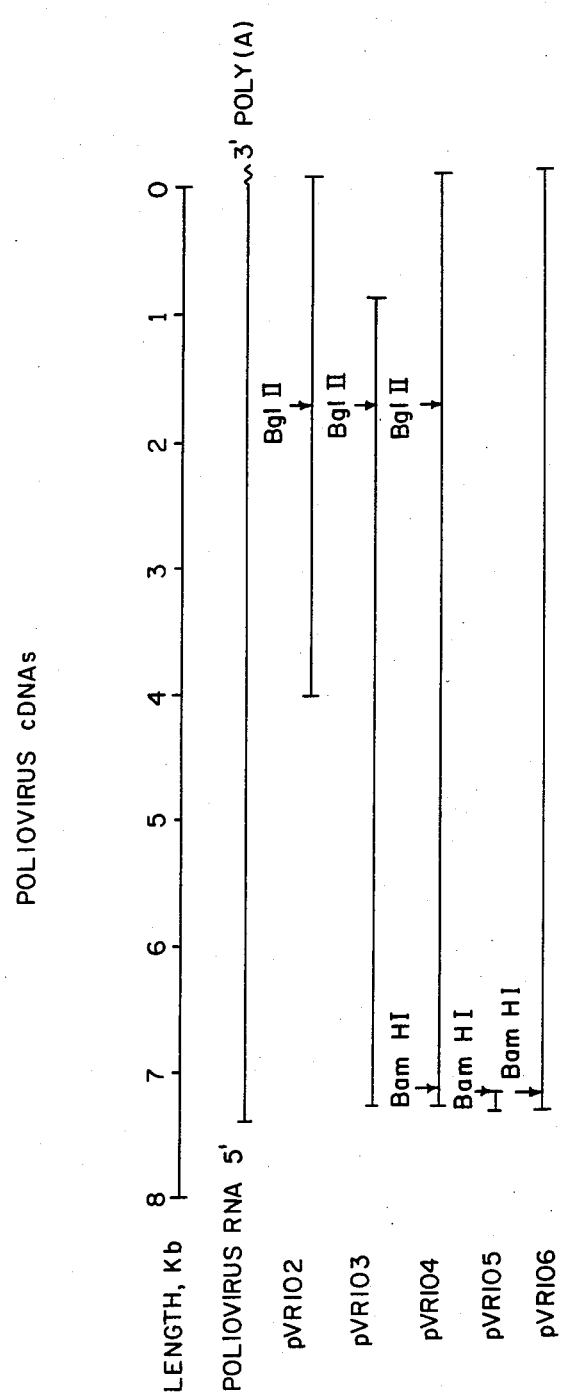
FIG. 3 is a schematic diagram illustrating the length of separate poliovirus ds cDNA's produced according to this invention.

The methods outlined in Example 1 were employed to generate two poliovirus cDNA's of 4.0 Kbp and 6.5 Kbp insert length. A diagram of these DNA's is shown in FIG. 3, wherein they are designated pVR102 and pVR103. A full poliovirus RNA chain is also illustrated for purposes of comparison DNA of both plasmids pVR102 and pVR103 was cleaved by incubation at 37° in a 0.1 ml reaction mixture containing 15 mM Tris HCl (pH 7.4), 5 mM MgCl$_2$, 50 mM NaCl, DNA [500 ug/ml] and a mixture of restriction endonucleases EcoRI and Bgl II. After 60 minutes, the mixture was phenol extracted, ethanol precipitated and electrophoresed on a 1% agarose gel. The largest fragments of both clones resulting from this digestion were eluted from the gel and resuspended in 0.01 ml of H$_2$O. 0.002 ml of each of those DNA's was then added to a mixture containing 50 mM Tris HCl (pH 7.5), 10 mM MgCl$_2$, 1.0 mM ATP and 300 units of phage T4 DNA ligase. The reaction mixture was incubated at 15° for 16 hours. After this time, 0.002 ml of the mixture was used to transform E. coli bacteria as described above. Resulting tetracycline-resistant colonies were examined by isolating plasmid DNA as previously described. Cleavage of the plasmid DNA's with various restriction enzymes and analysis of the digests on agarose gels indicated that a near-full length poliovirus cDNA clone had been constructed. This clone (pVR104), which is illustrated in FIG. 3, begins at the 3' poly(A) sequence of poliovirus RNA, contains all internal sequences and ends 115 bases from the 5' end of the viral RNA.

EXAMPLE 3

Construction of Plasmid pVB105

1. Isolation of Primer

To construct a plasmid representing the 5' end of poliovirus RNA, the technique of primer extension was employed. Plasmid pVR103 was used to isolate a primer in the following way. Plasmid DNA (100 μg of pVR103) was digested with restriction endonucleases Bam HI and Bgl II. The digestion products were separated by polyacrylamide gel electrophoresis and the slowest migrating fragment was extracted from the gel. This DNA fragment, which consisted of bases 375-3607 of pBR322 linked, at the Pst I site, to DNA representing bases 116-220 of the poliovirus genome, was treated with calf alkaline phosphatase to remove 5'-terminal phosphates. The DNA was then (phosphorylated at its 5' ends with $^{32}$P using γ-$^{32}$P-ATP and polynucleotide kinase. The phosphorylated fragment was then cleaved with restriction endonuclease RsaI, and the cleavage products were separated by polyacrylamide gel electrophoresis. A 74-base fragment from the Bam HI site (position 220) to the Rsa I site (position 149) was purified from the gel. This fragment contained $^{32}$P at the Bam HI site only, and served as the end-labeled primer.

2. Primer Extension

The labeled primer was hybridized with 2 μg of purified poliovirus RNA in the following way. The primer and viral RNA were combined in a total volume of 0.005 ml, boiled for 2 minutes, and quenched in dry ice. The mixture was then adjusted to 0.01 M Pipes.HCl pH 6.4, 0.4 M NaCl, 2 mM EDTA, 80% formamide in a total volume of 0.05 ml. This mixture was held at 42° for 4 hours and then diluted to 0.2 ml with water and precipitated with three volumes of ethanol. The mixture was reprecipitated with ethanol three additional times to remove residual formamide.

The final ethanol pellet was resuspended in a 0.05 ml reaction mixture containing 50 mM Tris.HCl pH8.3, 50 mM KCl, 0.5 mM dithiothreitol (DTT), 10 mM MgCl$_2$, 40 μg/ml actinomycin D, and 0.5 mM each of deoxyadenosine triphosphate, deoxycytidine triphosphate, deoxyguanosine triphosphate, and deoxythymidine triphosphate. Reverse transcriptase (RNA-dependent DNA polymerase) was added, and the mixture was incubated at 42° for 60'. After this time, the mixture was made 0.3N NaOH, incubated 37° for three hours, neutralized and the reaction contents were precipitated with ethanol. The reaction products were separated on an 8% polyacrylamide gel containing 6M urea. An autoradiograph of the gel revealed that the 74-bp primer had been extended to 220 bases in length, indicating that the reverse transcriptase had most likely extended to the first base of the viral RNA. Nucleotide sequence analysis of the primer-extended material confirmed that the extended product reached the very 5' end of the viral RNA.

3. Molecular Cloning of Primer Extended Material

The primer-extended band 220 bases in length was excised and purified from the 8% polyacrylamide gel (see above). The fragment was ethanol precipitated and suspended in a 0.1 ml mixture containing 1 mM CoCl$_2$, 0.14 M cacodylic acid, 0.2 mM DTT, 0.15 mM dCTP, 0.3 mg/ml bovine serum albumin and the enzyme terminal deoxynucleotidyl transferase. After incubation at room temperature for 20', the reaction mixture was extracted with phenol and ethanol precipitated. This treatment added a stretch of d(C) residues to the 3' end of the primer-extended fragment.

The oligo d(C)-tailed fragment was then made double-stranded using a primer of oligo d(G)$_{2-18}$ and DNA polymerase I (Klenow). The fragment was incubated in a 0.1 ml mixture containing 0.1 M Tris.HCl pH 7.5, 0.2 M MgCl$_2$, 0.1 M DTT, 1 mM each dCTP, dATP, dTTP, dGTP, 20 μg/ml oligo d(G) and the Klenow fragment of DNA polymerase I. After incubation at 37° for 60', the reaction mixture was extracted with phenol and applied to a 0.5 cm×5 cm column of Sephadex G-100 equilibrated and developed with 0.1 M NaCl, 10 mM Tris.Cl pH 7.5, 1 mM EDTA. The void fractions were pooled and ethanol precipitated. The resulting material was subjected to a terminal transferase reaction (see above) to add stretches of oligo d(C) to its 3' ends. These tiled molecules were then cloned into the Pst I site of plasmid pBR322 using techniques described in Example 1. By using tails of oligo d(C) to clone this fragment, the Bam HI site, which had been phosphorylated for primer extension, was restored. Tetracycline-resistant colonies obtained from transformation of this material into E. coli were therefore screened for cleavage with Bam HI. Several molecular clones were isolated which contained inserts approximately 220 bases long which were excisable with Pst I plus Bam HI. Nucleotide sequence analysis of one such clone, called pVR105, indicated that it contained DNA representing bases 1-220 of the viral RNA. Plasmid pVR105 is illustrated in FIG. 3.

EXAMPLE 4

Construction of pVR106 and pVR106a, Full-Length Poliovirus ds cDNA Plasmids

Figure 4:
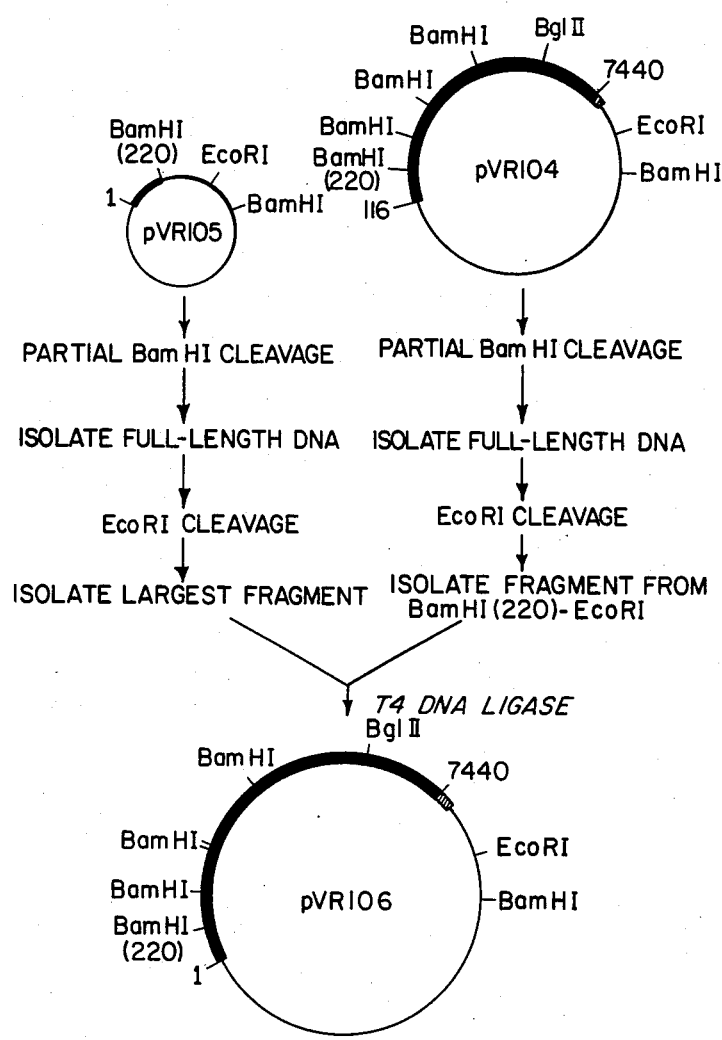
FIG. 4 is a schematic diagram illustrating the method employed to splice two poliovirus ds cDNA's (pVR104 and pVR105) to produce a full-length poliovirus ds cDNA (pVR106)

The procedure employed for joining plasmids pVR104 and pVR105 to form a full-length copy of poliovirus ds cDNA in pBR322 in shown in FIG. 4.

Conditions for partial Bam HI cleavage of plasmid pVR104 were determined by incubating the plasmid with enzyme at 37° for increasing periods of time. Digests were analyzed by electrophoresis in 0.6% agarose gels and examined for the presence of linear full-length molecules. The incubation time which gave reasonable yield of linear full-length molecules (which, by definition, are a permutation of molecules cut once by Bam HI) was used to digest 100 μg of pVR104. The digestion products were electrophoresed on an 0.6% agarose gel and the linear, full-length molecules were excised and recovered from the gel. These molecules were then cleaved with EcoRI and the cleavage products were separated by 0.6% agarose gel electrophoresis. An 8-Kb DNA fragment from base 220 of the viral genome through the 3' end of the genome and extending to the pBR322 EcoRI site was identified by its size and extracted from the agarose gel.

Similarly, plasmid pVR105 was digested under conditions which yielded linear, full-length molecules, as judged by 0.6% agarose gel electrophoresis. Linear molecules were purified by gel electrophoresis and cleaved with EcoRI. The cleavage products were separated by 0.6% agarose gel electrophoresis. The fragment consisting of nucleotides 1-3607 of pBR322 united to DNA representing bases 1-220 of the poliovirus genome was identified by its size and purified.

Approximately 0.1 μg of the DNA fragments isolated from pVR104 and pVR105 (see above) were mixed and incubated in a reaction mixture containing 50 mM Tris.HCl pH 7.8, 10 mM NgCl$_2$, 20 mM DTT, 1 mM ATP. T4 DNA ligase was added and the mixture was incubated 18 hours at 15° C. After this time, the ligated DNA's were transformed into E. coli C600 as described previously. Tetracycline-resistant colonies were examined for the presence of a full-length poliovirus cDNA clone by cleavage of plasmid DNA with various restriction endonucleases. For example, a full-length clone cleaved with Kpn I and examined by 0.6 % agarose gel electrophoresis would be expected to generate fragments 8200, 2998 and 596 bases in length. Two clones were identified, pVR106 and pVR106a, which, when digested with enzymes Bam HI, KpnI, PstI, BglI, BglII and XbaI, yielded patterns consistent with those expected from a full-length clone. Nucleotide sequence analysis of the 5' end of the insert from pVR106 and pVR106a proved that the 5' end of the viral RNA was present in these molecular clones. Therefore, pVR106 and pVR106a contained a full-length cDNA copy of the poliovirus genome at the PstI site of pBR322.

A deposit of a bacterial cell line containing plasmid pVR106 has been made at the American Type Culture Collection and is identified by ATCC Accession No. 31844. This deposit consists of plasmid pVR106 in the bacterial host E. coli HB101. The plasmid was inserted into this bacterial strain, which is rec A$^-$, to maintain its stability. Transformation was achieved employing the procedures described in Example 1, Section 3c.

EXAMPLE 5

Sequencing of Poliovirus cDNA

The complete nucleotide sequence of the poliovirus cDNA specific insert in clone pVR106 was obtained using published techniques. See Maxam, A. M. and Gilbert, W., (1980), in Methods in Enzymology, Grossman, L. and Moldave, K., eds., Vol. 65, pp 499–559, Academic Press, New York. This sequence in shown in FIG. 5.

In the 5' untranslated region, potential termination codons are marked by asterisks and the phase in which they occur is indicated. ATG codons in the untranslated region are underlined, and the phase in which they occur is shown. The sequence is translated into amino acids starting at base 743 through base 7339. The coding region and amino acid sequence of VPg, the protein linked to the 5' end of the viral RNA, are indicated by underlining. The location of VPg is based on the published sequence. See Larsen, G. R., Semler, B. L. and Wimmer, E., J. Virol. 37, 328–335 (1981). The positions of the virion proteins are indicated on the basis of amino acid sequence data.

EXAMPLE 6

Transfection of Cells With Full-Length Poliovirus Clone

CV-1 and HeLa cells were grown to 80% confluence in 10-cm plastic dishes. Briefly, the cells were grown in Dulbecco's modified Eagle medium (DMEM) containing 10% calf serum. Cells were maintained at 37° C. in a humidified incubator containing an atmosphere supplemented with 5% CO$_2$.

Cells-were transfected with either 10 μg plasmid DNA per dish or 2 μg of viral RNA prepared as described in Example 1. Transfection was achieved using the modified calcium-phosphate technique described by Parker and Stark. See B. A. Parker and G. R. Stark, *J. Virol.*, 31, 360 (1979). Briefly, medium was removed from the cells, and DNA was added as a calcium-phosphate precipitate in Hepes-buffered saline. After 20 minutes at room temperature, cells were covered with warm medium (Dulbecco's modified Eagle medium plus 10% calf serum) and incubated four hours at 37°. After this time, medium was removed, cells were washed once with warm medium, and 2.5 ml per dish of 15% glycerol in Hepes-buffered saline was added. After 3.5 minutes at 37° C., the glycerol was removed and cells were washed once with warm medium. One of the duplicate dishes was then covered with warm medium, and the other was covered with medium containing 1% agarose (Sigma). Plates were incubated at 37° C. for 4–5 days. To count plaques, the agar overlay was removed and cells were stained with 0.1% crystal violet in 50% ethanol. Medium from cells incubated under liquid was assayed for infectious poliovirus on HeLa cell monolayers.

The results are shown in Table 2, wherein virus titers shown are values for typical experiments.

For RNAse treatment, 5 μg of boiled pancreatic RNAse (Worthington) were used for 10 μg DNA or 2 μg RNA.

As can be seen, a high virus titer was found in the medium from cells transfected with pVR106 but no virus was released from pBR322-transfected cells. Cells transfected with pVR106 and incubated under agar displayed, upon staining with crystal violet, plaques similar to those induced by poliovirus. No plaques were observed on cells transfected with pBR322 DNA. Usually, from 10–70 plaques were observed per 100 mm plate of cells transfected with 10 μg of pVR106. If approximately 10% of the cells receive DNA, as suggested by Parker and Stark, then infectious foci arose at an efficiency of about $2-8 \times 10^{-5}$.

Transfection with an independently-derived, full-length poliovirus cDNA clone, designated pVR106a, (see Example 4), also yielded infectious virus following transfection into cells.

Further experiments, the results of which are also presented in Table 2, illustrated that virus production in transfected cells was directed by plasmid pVR106. No virus was detected in cells transfected with pVR106 DNA cleaved by Hinf I, an enzyme which cuts the plasmid at 45 sites and which does not reduce the infectivity of viral RNA. The infectivity of pVR106 DNA was not significantly reduced by treatment with RNAse under conditions which abolish the infectivity of viral RNA. Therefore, infectivity was not due to viral RNA contaminating the pVR106 DNA. Phenol extraction of pVR106 DNA alone or followed by RNAse treatment did not lower the infectivity of the plasmid. Thus, virions did not appear to be present in the pVR106 preparation. When pVR106 DNA was assayed directly for contaminating virions on HeLa cell monolayers, no infectivity was detected (data not shown). These results indicate that the infectivity of pVR106 is inherent in the plasmid DNA.

TABLE 1

Transfection of Cultured Mammalian Cells With Various Plasmid DNA's

| Nucleic Acid | Plaque forming units/ml in medium | No. of plaques on transfected cell monolayers |
|---|---|---|
| CV-1 cells | | |
| pVR106 | $1.2 \times 10^9$ | 22 |
| pVR106 + Hinf I | 0 | 0 |
| pVR106 + RNAse | $1.3 \times 10^9$ | 10 |
| pVR106, phenol extracted | $1 \times 10^9$ | 22 |
| pVR106, phenol extracted, then RNAse | $1.4 \times 10^9$ | 26 |
| pBR322 | 0 | 0 |
| viral RNA | $1.5 \times 10^9$ | 71 |
| viral RNA + RNAse | 0 | 0 |
| viral RNA + Hinf I | $1.4 \times 10^9$ | 20 |
| HeLa cells | | |
| pVR106 | $3.7 \times 10^8$ | 69 |
| pBR322 | 0 | 0 |

EXAMPLE 7

Antibody Neutralization Test

The identity of the virus produced in pVR106-transfected cells was examined employing an antibody neutralization test. About 100 plaque-forming units of the virus released into the culture medium of pVR106 transfected cells obtained following the procedures of Example 6 was mixed with various dilutions of rabbit anti-poliovirus antiserum and assayed for infectivity. In parallel, 100 plaque-forming units of authentic poliovirus was assayed for neutralization by the serum. Both viruses were neutralized 50% by a 1/50,000 dilution of the serum indicating that the pVR106-derived virus was authentic poliovirus.

EXAMPLE 8

Transfection of Cells With Poliovirus clone pVR104

Plasmid pVR104, prepared as described in Example 2 above, contains an almost full-length cDNA sequence for the entire poliovirus genome, but lacks the first 115 bases of poliovirus genome. Plasmid pVR104 was transfected into CV-1 cells following the procedures of Example 6 but did not result in virus production indicating that the 5' end of the poliovirus RNA is required for infectivity even though it does not encode protein (there are no AUG codons in this region).

Industrial Applicability

The invention described herein is useful in the production of RNA viral cDNA, such as poliovirus cDNA, by recombinant DNA techniques. The products, such as poliovirus cDNA, are in turn useful in assays for the detection of such viruses and in the production of viral antigens and antibodies against such viruses, etc.

Equivalents

Those skilled in the art will recognize, or be able to ascertain, using no more than routine experimentation, many equivalents to the specific embodiments of the invention described herein. Such equivalents are intended to be encompassed by the following claims.

We claim:

1. A method for producing infectious poliovirus cDNA comprising:

a. reverse transcribing poliovirus sequences to provide essentially full-length poliovirus cDNA;
b. inserting said cDNA into a recombinant DNA vector;
c. transforming cells in which said recombinant DNA vector will multiply;
d. cloning a transformed cell to produce a clonal cell line capable of replicating said cDNA;
e. culturing said clonal cell line under conditions whereby essentially full-length and infectious poliovirus cDNA is produced; and
f. harvesting said infectious poliovirus cDNA from said cell culture.

2. A method of claim 1 wherein recombinant DNA vector comprises a vector selected from a bacterial plasmid, a phase, an animal virus, or a yeast vector.

3. A method for the bacterial production of infectious poliovirus cDNA, comprising:
a. reverse transcribing poliovirus RNA to provide essentially full-length ss poliovirus cDNA;
b. forming ds cDNA from said ss poliovirus cDNA;
c. inserting said ds poliovirus cDNA into a bacterial plasmid to create a chimeric plasmid;
d. transforming bacterial cells with said chimeric plasmid;
e. cloning a transformed bacterial cell to produce a clonal bacterial cell line capable of replicating said poliovirus ds cDNA;
f. culturing said clonal bacterial cell line in cell culture under conditions conductive to the production of essentially full-length and infectious poliovirus ds cDNA; and
g. harvesting said infectious poliovirus ds cDNA from said cell culture.

4. A method of claim 3 wherein said bacterial cells comprise *E. coli* cells.

5. A method of claim 4 wherein said bacterial plasmid contains a selective marker for transformed cells.

6. A method of claim 5 wherein said selective marker is resistance to an antibiotic.

7. A method of claim 6 wherein said bacterial plasmid comprises plasmid pBR322.

8. Infectious poliovirus ds cDNA produced by a method of claims 3, 4, 5, 6, or 7.

9. A recombinant DNA vector containing infectious poliovirus cDNA.

10. A chimeric bacterial plasmid containing infectious poliovirus cDNA.

11. A clonal cell line transformed with a recombinant DNA vector containing infectious poliovirus ds cDNA.

12. A clonal bacterial cell line transformed with a chimeric plasmic containing infectious poliovirus ds cDNA.

13. A clonal bacterial cell line of claim 12 wherein said bacterial cells comprise transformed E. coli cells.

14. The clonal bacterial cell line identified by ATCC Accession No. 31844.

15. Plasmid pVR106.

16. A recombinant DNA vector containing a full-length poliovirus cDNA.

17. Poliovirus cDNA having the base sequence set forth in FIG. 5 and equivalents thereto containing different codons for the same amino acid sequences or equivalent sequences.

18. Infectious poliovirus cDNA.

19. A method for producing infectious poliovirus, comprising:
a. transfecting cells with infectious cDNA for said poliovirus;
b. culturing said cells under conditions sufficient for the cellular production of poliovirus; and,
c. harvesting said poliovirus.

20. A method of claim 18 wherein said cells comprise mammalian cells.

21. A method of claim 19 wherein said mammalian cells are human cells.

* * * * *

UNITED STATES PATENT AND TRADEMARK OFFICE
CERTIFICATE OF CORRECTION

PATENT NO. : 4,719,177
DATED : January 12, 1988
INVENTOR(S) : David Baltimore and Vincent R. Racaniello It is certified that error appears in the above—identified patent and that said Letters Patent is hereby corrected as shown below:

Claim 2, line 16 the word "phase" should read --- phage ---.

Claim 3, line 30 the word "conductive" should read --- conducive ---.

Claim 6, line 2 "resistance" should read --- resistant ---.

Claim 12, line 14 the word "plasmic" should read --- plasmid ---.

Claim 13, line 17 the word "E. coli" should be italicized --- *E. coli* ---.

Claim 20, line 35 the phrase "claim 18" should read --- claim 19 ---.

Claim 21, line 37 the phrase "claim 19" should read --- claim 20 ---.

Signed and Sealed this

Twenty-second Day of November, 1988

Attest:

DONALD J. QUIGG

*Attesting Officer*  *Commissioner of Patents and Trademarks*